(12) United States Patent
Jordan

(10) Patent No.: US 8,785,504 B2
(45) Date of Patent: Jul. 22, 2014

(54) 4-HYDROXY BENZOATE DERIVATIVES FOR USE IN THE TREATMENT OF INFECTION, INFLAMMATION OR PAIN

(76) Inventor: Roy Arlington Jordan, Guilford (GB)

( * ) Notice: Subject to any disclaimer, the term of this patent is extended or adjusted under 35 U.S.C. 154(b) by 729 days.

(21) Appl. No.: 12/663,451

(22) PCT Filed: Jun. 12, 2008

(86) PCT No.: PCT/GB2008/002001
§ 371 (c)(1),
(2), (4) Date: May 25, 2010

(87) PCT Pub. No.: WO2008/155520
PCT Pub. Date: Dec. 24, 2008

(65) Prior Publication Data
US 2010/0292329 A1    Nov. 18, 2010

(30) Foreign Application Priority Data
Jun. 20, 2007   (GB) .................................. 0711947.2

(51) Int. Cl.
*A01N 31/08*   (2006.01)
*A61K 31/05*   (2006.01)
*A01N 33/18*   (2006.01)
*A61K 31/04*   (2006.01)

(52) U.S. Cl.
USPC ......................................... 514/731; 514/740

(58) Field of Classification Search
None
See application file for complete search history.

(56) References Cited

U.S. PATENT DOCUMENTS 6,027,719 A * 2/2000 Tomura et al. ............. 424/78.02
6,120,779 A * 9/2000 Nayak et al. .................. 424/401

FOREIGN PATENT DOCUMENTS

WO   WO 2007014514 A2 *   2/2007

\* cited by examiner

*Primary Examiner* — Jeffrey S. Lundgren
*Assistant Examiner* — Michael Schmitt
(74) *Attorney, Agent, or Firm* — Meyertons, Hood, Kivlin, Kowert & Goetzel, P.C.; Eric B. Meyertons

(57) ABSTRACT

A compound of the general formula (I) is provided for use in the topical treatment of infection, inflammation and/or pain: wherein $R^1$ independently represents a methylene group, an ethylene group or a straight or branched chain $C_3$ to $C_6$ alkylene group; $R^2$ independently represents a hydrogen atom, a methyl group, an ethyl group or a straight or branched chain $C_3$ to $C_{20}$ alkyl group; x represents 0 or an integer from 1 to 4 and y represents 0 or an integer from 1 to 4, wherein the sum of x and y is 4; and Z represents a hydrogen atom or $(HOR^1)_y R^2_x N^+$; compositions including the compound; use of the compound in the manufacture of a medicament; and methods of medical treatment including the topical application of the compound.

8 Claims, No Drawings

4-HYDROXY BENZOATE DERIVATIVES FOR USE IN THE TREATMENT OF INFECTION, INFLAMMATION OR PAIN

BACKGROUND OF THE INVENTION

1. Field of the Invention

The invention generally provides compounds and compositions for use in the topical treatment of infection, inflammation or pain, a method of preparing the compounds, uses of the compounds and compositions in the preparation of medicaments for the topical treatment of infection, inflammation or pain, and a method of topical treatment of infection, inflammation or pain using the compounds and compositions.

2. Description of the Relevant Art

There are many common human or animal conditions which result in infection, inflammation and/or pain for which there are limited or no effective preventative or curative treatment. These include allergic and non-allergic conditions such as eczema, acne, psoriasis, geographic tongue and adverse reactions to insect bites (e.g., flea or midge bites). In some instances, steroidal treatments may be applied to the skin of a patient to treat these conditions with limited success and often with adverse side effects.

A way of ameliorating the above-identified problems has been sought.

SUMMARY OF THE INVENTION

A compound of the general formula (I) may be used in the topical treatment of infection, inflammation and/or pain:

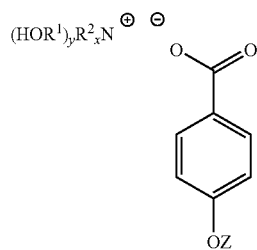

wherein $R^1$ independently represents a methylene group, an ethylene group or a straight or branched chain $C_3$ to $C_6$ alkylene group; $R^2$ independently represents a hydrogen atom, a methyl group, an ethyl group or a straight or branched chain $C_3$ to $C_{20}$ alkyl group; x represents 0 or an integer from 1 to 4 and y represents 0 or an integer from 1 to 4, wherein the sum of x and y is 4; and Z represents a hydrogen atom or $(HOR^1)_y R^2_x N^+$. Compositions including the compound of general formula (I); use of the compound of general formula (I) in the manufacture of a medicament; and methods of medical treatment including the topical application of the compound of general formula (I) are also described.

DETAILED DESCRIPTION OF THE PREFERRED EMBODIMENTS

It is to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

In one embodiment, a compound of the general formula (I) is provided for use in the topical treatment of infection, inflammation and/or pain:

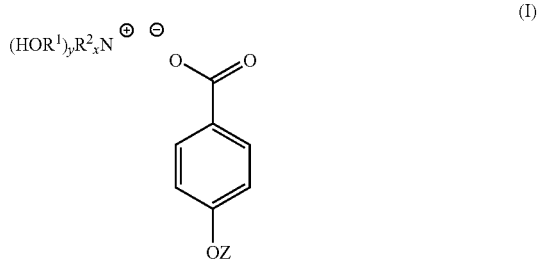

wherein $R^1$ independently represents a methylene group, an ethylene group or a straight or branched chain $C_3$ to $C_6$ alkylene group; $R^2$ independently represents a hydrogen atom, a methyl group, an ethyl group or a straight or branched chain $C_3$ to $C_{20}$ alkyl group; x represents 0 or an integer from 1 to 4 and y represents 0 or an integer from 1 to 4, wherein the sum of x and y is 4; and Z represents a hydrogen atom or $(HOR^1)_y R^2_x N^+$.

It has been surprisingly found that the compound of the general formula (I) can provide beneficial therapeutic effects when applied topically to a human or animal patient by ameliorating, curing, preventing and/or remedying a condition associated with infection, inflammation and/or pain. Such conditions include a disorder of the non-vascular and/or vascular dermis of a human or animal including the oral membrane and/or the nasal membrane and/or the bronchial membrane, the surface membrane of the tongue or body tissue exposed during a surgical procedure.

By infection, in some aspects it is meant a parasitic, viral or bacterial infection. By an animal, in some aspects it is meant a mammal, in particular a domestic mammal such as a horse.

In some aspects, $R^2$ can be a hydrogen atom, a methyl group, an ethyl group and/or a straight or branched chain $C_3$ to $C_8$ alkyl group. In some aspects, $R^1$ can be a methylene, ethylene or propylene group, $R^2$ can be a hydrogen atom, a methyl, ethyl or propyl group and Z can be a hydrogen atom. In one aspect, the compound of the general formula (I) may have substituents where $R^1$ is an ethylene group, $R^2$ is a hydrogen atom, x is 1, y is 3, and Z is a hydrogen atom.

In some aspects the compound according to Formula (I) can be monoethanolammonium 4-hydroxybenzoate, diethanolammonium A-hydroxybenzoate, triethanolammonium 4-hydroxybenzoate, tetraethanolammonium 4-hydroxybenzoate, cetyltrimethylammonium A-hydroxybenzoate or bis (triethanolammonium) 4-oxybenzoate.

In some aspects, the compound of the general formula (I) is for use in the treatment of a condition associated with topical infection, inflammation or pain. Such a condition can be a human condition such as eczema, psoriasis, acne, sunburn, a wound (such as that caused by an explosion), bruising, a burn, gout, ringworm, a cold sore, impetigo, a symptom associated with the common cold or influenza, hay fever, sinusitis, gum disease, cystic fibrosis, epidermolysis bullosa, bacterial infection or geographic tongue, or an adverse reaction to an insect bite such as a flea bite. Otherwise, the condition may be an animal condition such as sweet itch, which is a reaction to a midge bite and which can in particular affect a horse.

It is believed that the compound of the general formula (I) may assist in dispersing or preventing fluid build-up in injured body tissue. Accordingly, the compound of the general formula (I) may also be useful in the treatment of conditions where there is a build up of body fluids. Such conditions may include cystic fibrosis or post-operative swelling, in particular facial swelling after plastic surgery or other physical injury such as that caused by road trauma or a sports injury.

In some aspects, the compound of the general formula (I) can be used for the treatment of conditions associated with infection, inflammation or pain by itself without a diluent, as the compound dissolved in aqueous solution and/or in conjunction with non-aqueous pharmaceutically acceptable diluents. In some aspects, the compound can be incorporated into a cosmetic skin treatment product such as a moisturizer or a beauty lotion.

According to an embodiment, there is also provided a pharmaceutical composition including a compound according to Formula (I) in association with a pharmaceutically acceptable diluent. Optionally, the diluent may be a pharmaceutically acceptable carrier.

In some aspects, the composition is a formulation for topical application to a human or animal.

For the pharmaceutically acceptable diluent, any diluent may be used which is compatible with the human and/or animal skin, oral membrane, bronchial membrane or nasal membrane. Where the diluent is a carrier, any pharmaceutically acceptable carrier may be used which may enhance the ability of the compound of the general formula (I) to penetrate the skin barrier or the oral membrane or the nasal membrane or the bronchial membrane.

A suitable diluent for use in the compositions may include water; an alcohol such as ethanol, n-propanol, 2-propanol, t-butyl alcohol; an ether such as methyl t-butyl ether (MTBE); a ketone such as acetone, methyl ethyl ketone; a humectant such as glycerol (glycerine); a glycol such as ethylene glycol, propylene glycol; an emulsifier such as a polyhydric $C_1$ to $C_5$ alcohol partially esterified with a long-chain ($C_{12}$ to $C_{24}$) fatty acid such as glycerol monostearate, isopropyl myristate, a fatty acid ester of a sugar alcohol such as sorbitan mono-fatty acid ester, a polyethoxylated derivative of such compounds, a polyethoxyethylene fatty acid ester and a fatty alcohol ether, cholesterol, cetyl stearyl alcohol, a wool wax alcohol and a synthetic surfactant with a low hydrophilic-lipophilic balance (HLB) value; a solubiliser such as carbopol; a low-viscosity paraffin, a triglyceride; a lipophilic substance such as isopropyl myristate; a pH regulator such as tetraethyl ammonium bromide (TEA), a carbonate, a phosphate; a chelating agent such as ethylenediamine tetraacetic acid (EDTA) and a salt thereof; and/or a preservative.

The pharmaceutical composition may contain a cosmetic excipient. Such a cosmetic excipient is well known to the person skilled in the art of pharmaceutical formulations and may be selected from a humectant, a smoothing agent, a UV filter, a pigment, a dye, a perfume, a vitamin and/or a bleaching agent.

In some aspects, the composition may include a commercially-available skin treatment product. Such a commercially-available skin treatment product may be a product sold under the name Vaseline Intensive Care Dry Skin Lotion, Oil of Olay Active Beauty Fluid or Boots Aqueous Cream B.P. or other similar product.

Vaseline Intensive Care Dry Skin Lotion is a formulation that includes fragrance(s)/perfume(s), glycerin, stearic acid, retinyl palmitate, methylparaben, triethanolamine, glycol stearate, glyceryl stearate, 2,6-di-t-butyl-p-cresol (BHT), disodium EDTA, octyl methoxycinnamate, DMDM hydantoin (1,3-dimethylol-5,5-dimethyl hydantoin), tocopheryl acetate, water, sunflower seed oil/extract, corn oil, lecithin, carbomer, Dimethicone 350, attapulgite, titanium dioxide, cetyl alcohol, 3-iodo-2-propynylbutylcarbamate, soy sterol, stearamide AMP and color ant/pigment/dye(s).

Oil of Olay Active Beauty Fluid is a formulation that includes fragrance(s)/perfume(s), acrylates/$C_{10}$ to $C_{30}$ alkyl acrylate cross-polymer, glycerin, stearic acid, tetrasodium EDTA, cetyl palmitate, potassium hydroxide, glyceryl hydroxystearate, 1-naphthalenesulfonic acid (FD&C Red #4 (Cl 14700)), water, petrolatum, carbomer, polyoxyethylated stearyl alcohol (Steareth 2), Dimethicone 350, octyldodecyl myristate, cetyl alcohol and mineral oil.

Boots Aqueous Cream B.P. is a formulation that includes liquid paraffin, white soft paraffin, emulsifying wax, water and chlorocresol.

In some aspects, the compound of the general formula (I) may be present at up to 60% by weight of the composition or between 10 to 55% by weight of the composition, particularly where the composition is an aqueous composition. In some aspects, the compound may be present at up to 15% by weight of the composition, particularly where a nonaqueous pharmaceutically acceptable carrier is also employed in the composition. In some aspects, the compound may be present at 0.2 to 10% by weight or 0.5 to 5% by weight of the composition. In some aspects, the compound of the general formula (I) may be present in a composition at 0.7, 0.9, 2, 3, 10, 30 or 50% by weight of the composition.

The dosage of the compound of the general formula (I) applied in treatment may generally be established by a person skilled in the art. In some aspects, the composition may be liberally applied as required to an area of a human or animal patient requiring treatment.

There is also provided a method of preparing a compound according to Formula (I) that includes:

(i) when at least one of $R^2$ of Formula (I) is a hydrogen atom and x represents an integer from 1 to 4, reacting a compound of formula (II)

wherein A is a hydrogen atom or a cation of the formula $(HOR^1)yR^2_xN^+$ wherein $R^1$, $R^2$, x and y are as defined above with a compound of formula (III)

wherein $R^3$ independently represents a methylene group, an ethylene group or a straight or branched chain $C_3$ to $C_6$ alkylene group; $R^4$ independently represents a hydrogen atom, a methyl group, an ethyl group or a straight or branched chain $C_3$ to $C_{20}$ alkyl group; a is zero or an integer from 1 to 3, b is zero or an integer from 1 to 3, wherein the sum of a and b is 3; or (ii) reacting a compound of formula (IV)

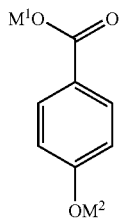

(IV)

wherein $M^1$ represents a cation and $M^2$ represents a cation or a hydrogen atom,
with a compound of fonnula (V)

$$[N(R^1OH)_y R^2{}_x]X \qquad (V)$$

wherein $R^1$, $R^2$, x and y are as defined for the compound of Formula (I) and X is an anion.

In some aspects of the method, the reactants can be prepared in solution prior to reacting or used by themselves. When a solution is used, a suitable solvent includes a polar solvent such as water, acetone and/or an alcohol.

In some aspects of option (ii) of the method, $M^1$ and/or $M^2$ may be an alkali metal cation such as a potassium or sodium cation. In some aspects, X may be a halide anion such as a fluoride, chloride or bromide anion. The reaction according to option (ii) of the method is understood to proceed via a metathesis reaction wherein a by-product of the reaction is a compound according to the formula MX, which in some aspects may be the alkali metal salt of a halide anion.

There is also provided a compound for use in the topical treatment of infection, inflammation and/or pain obtainable from the method of preparation according to the invention.

There is also provided the use of a compound according to Formula (I) or a composition including a compound according to Formula (I) in the preparation of a medicament for the topical treatment of infection, inflammation and/or pain There is also provided a method of topical treatment of infection, inflammation and/or pain in a human or an animal the method including the application of therapeutically effective amount of a compound according to Formula (I) or a composition including a compound according to Formula (I) to a human or animal in need of such treatment.

In some aspects of the method of treatment, the compound of the general formula (I) may be applied to the human or animal by itself or as a composition which is applied topically to an area of the human or animal affected by infection, inflammation or pain. In some aspects, the compound of the general formula (I) may be applied as an aqueous solution which is sprayed on to an affected area of the human or animal. Spraying means may include a nasal spray such as an atomizer. An atomizer may be used for administration of the compound or composition to the bronchial membrane. In other aspects, the compound may be applied topically by manually rubbing the composition into the affected area.

In some aspects of the method of treatment, the method may include topical application of a compound of the general formula (I) or composition including a compound of the general formula (I) to an area of a human or animal as a pre-treatment to prevent the development of a condition associated with infection, inflammation or pain. In some aspects, the compound or composition may be applied post-surgery. In some aspects, the method of treatment is a surgical treatment. In some aspects, where the method of treatment is surgical treatment, the compound or composition is sprayed onto the area to be treated.

The embodiments are illustrated by the following Examples which are not intended to limit the scope of the claims.

Infrared spectra were recorded in KBr disc on a Perkin Elmer 2000 Fourier Transform Infrared Spectrophotometer. $^1$H NMR spectra were recorded in $D_2O$ on a Bruker AV300 (300 MHz) NMR spectrometer. Elemental analyses were obtained on a Leeman Labs Inc CE440 Elemental Analyser. Refractive indices were obtained on an Abbe Refractive Index Detector. pH measurements were obtained with an Aldrich glass pH electrode. Melting point (m.p.) data were determined on a Renhert 355272 melting point apparatus. Unless stated otherwise, all chemical reagents and solvents were obtained from Sigma-Aldrich Limited (Gillingham, Dorset, UK). Bacterial cultures were obtained from the University of Surrey, UK, Bacteriology Laboratory.

In examples 1 to 7, synthetic procedures are described for the preparation of compounds according to Formula (I). In example 8, various compositions including triethanolammonium 4-hydroxybenzoate (TEAB) are described. In examples 9 to 21, TEAB compositions were tested in vivo for efficacy on human patients suffering from various conditions. In example 22, TEAB compositions were tested on an animal patient susceptible to sweet itch. In example 23, in vitro testing is described relating to the antibacterial activity of TEAB. No side effects were observed as a result of the administration of a TEAB composition in the in vivo tests.

Example 1

Preparation and Characterisation of Triethanolammonium 4-hydroxybenzoate (TEAB)

4-hydroxybenzoic acid (10.6 g, 0.08 mol) was dissolved in acetone (200 mL). To the 4-hydroxybenzoic acid solution was added a solution of triethanolamine (9.23 g, 0.07 mol) dissolved in a water (70 mL)/acetone (200 mL) mixture yielding a clear solution. The solution was stirred at room temperature for 1 hour. The solution was stripped of acetone on a rotary evaporator to yield 91 g (100%) of a light yellow solution with n20d of 1.3890. This light yellow solution was found to contain 30% by weight of TEAB in water. A sample of the light yellow solution was reduced to near dryness yielding a white crystalline solid identified as TEAB containing 0.3 moles of water per mole of solid (93-94 C).

To establish the ionic nature of TEAB, 10 g of the light yellow TEAB solution was blended with water (300 mL) and Dowex MB-3 ion exchange resin (Dow Chemical Company) and left to stand overnight. At this time, the liquid component of the blend was separated from the resin and reduced to dryness resulting in no residue. This indicates that the anionic and cationic component of TEAB had been retained by the ion exchange resin and that the solution only contained TEAB.

Elemental analysis ($C_{13}H_{21}NO_6 \cdot 0.3H_2O$): Calculated (%) C 53.3, H 7.4, N 4.8, 0 34.4. Found (%) C 53.3, H 7.5, N 4.5, 0 34.7. $^1$H NMR($D_2O$):δ 3.4 (—$CH_2$-), 3.9(—$CH_2$-), 4.8 (NH), 4.8 (OH), 6.9 (ArH), 7.8 (ArH). Infrared spectroscopy, $cm^{-1}$:3450-3600(v(OH)), 2854(v(NH)), 1463(v(C=O)), 1377(v(C—O)). n20d (50% wt solution of TEAB in water) 1.4482. pH (50% wt solution of TEAB in water) 6.61. Calculated heat of reaction (kJ/mol)−12.0.

Example 2

Preparation of Triethanolammonium 4-hydroxybenzoate (TEAB)

Triethanolamine (149 g, 1 mol) was dissolved in water (287 mL). To this solution was added solid 4-hydroxybenzoic acid (138 g, 1 mol) over a period of 3 to 4 minutes. As the solid 4-hydroxybenzoic acid was added it reacted and dissolved increasing the temperature of the reaction mixture 5° C. After overnight standing, 573 g (100%) of a light yellow TEAB solution was recovered with n20d of 1.4484 and pH of 6.61. 40 g of the light yellow TEAB solution was reduced to 23 g on a rotary evaporator and this solution poured into acetone (300 mL). After 72 hours, a white crystalline solid was filtered off, washed with acetone and oven dried at 60° C. (m.p. 93-94 C). Yield 19 g.

Example 3

Preparation of Tetraethanolammonium 4-hydroxybenzoate 1-bromoethanol (100 g, 0.8 mol) and triethanolamine (119 g, 0.8 mol) were added to absolute ethanol (300 mL) and heated to 60 C while stirring. No apparent reaction was observed. After 2 weeks at room temperature stirring the reaction mixture contained a white crystalline solid which was filtered off, washed with ethanol and oven dried at 60 C to yield 5 g of tetraethanolammonium bromide (m.p. 189 C).

A 45% by weight aqueous solution of potassium hydroxide (100 g, 0.8 mol) was added to water (200 mL). To this solution with stirring was added 4-hydroxybenzoic acid (111 g, 0.8 mol). The mixture was stirred for 12 hours at room temperature to yield a white crystalline solid which was filtered off, washed well with acetone and dried. The white crystalline solid was potassium 4-hydroxybenzoate (m.p. 214 C).

Tetraethanolammonium bromide (4.58 g, 0.026 mol) and potassium 4-hydroxybenzoate (7.16 g, 0.026 mol) were dissolved in water (500 mL) at room temperature while stirring. After 30 minutes, acetone (250 mL) was added to the reaction mixture resulting in the precipitation of a white crystalline solid from the solution. The solid, identified as tetraethanolammonium 4-hydroxybenzoate contaminated with potassium bromide, was filtered off and washed well with acetone.

Example 4

Preparation of Diethanolammonium 4-hydroxybenzoate 4-hydroxybenzoic acid (10.6 g, 0.08 mol) was dissolved in acetone (200 mL). To the 4-hydroxybenzoic acid solution was added a solution of diethanolamine (8.4 g, 0.08 mol) dissolved in a water (70 mL)/acetone (200 mL) mixture yielding a clear solution. The solution was stirred at room temperature for 1 hour and the solution stripped of acetone on a rotary evaporator to leave 100 g of a colourless solution (100%). A sample of this colourless solution was further stripped to dryness to yield a white crystalline solid identified as diethanolammonium 4-hydroxybenzoate (m.p. 115 C).

Example 5

Preparation of Cetyltrimethylamnionium 4-hydroxybenzoate

Potassium 4-hydroxybenzoate (2.76 g, 0.02 mol) prepared according to the procedure as described in example 3 and cetyltrimethylammonium bromide (7.28 g, 0.02 mol) were added to water (200 mL) while stirring. The reaction mixture was heated to 70° C. to yield a clear solution. The mixture was allowed to cool to room temperature and maintained at that temperature for 12 hours whereupon a white crystalline solid precipitated. The white crystalline solid, identified as cetyltrimethylammonium 4-hydroxybenzoate (m.p. 111-113 C), was filtered off, washed well with acetone and dried in an oven at 60 C.

Example 6

Preparation of Bis(triethanolammonium) 4-oxybenzoate

To 48 mL of a stirred 48% by weight solution of TEAB (22 g, 0.08 mol) was added dropwise a 50 mL aqueous solution of triethanolamine (11.3 g, 0.08 mol). The reaction mixture was stirred at 80 C for 1 hour at which time the pH was 8.14. 10 g of this solution was poured into refluxing acetone (50 mL) to yield a clear solution which was allowed to cool to room temperature and then cooled at 6 C for 12 hours. A cream-coloured crystalline solid identified as bis(triethanolammonium) 4-oxybenzoate precipitated was filtered off (m.p. 93-95 C).

Example 7

Preparation of Bis(triethanolammonium) 4-oxybenzoate

In an alternative synthesis of bis(triethanolammonium) 4-oxybenzoate to Example 6, 4-hydroxybenzoic acid (9.7 g, 0.07 mol) was added to water (200 mL) and the mixture heated to reflux. An excess of triethanolamine (20.9 g, 0.14 mol) was added dropwise over 30 minutes and the reaction mixture heated at reflux for a further 1 hour. A cream-coloured crystalline solid believed to be his (triethanolammonium) 4-oxybenzoate (m.p. 93-95° C.) precipitated was filtered off and dried under reduced pressure.

Example 8

In the following Example, the preparation of nine compositions including TEAB for use in the topical treatment of infection, inflammation and/or pain are described. The constituents of compositions 1 to 9 are identified in Table 1 below.

TABLE 1

| Composition | Diluent | % by weight TEAB present |
|---|---|---|
| 1 | Water | 30 |
| 2 | Vaseline Intensive Care Dry Skin Lotion | 0.9 |
| 3 | Oil of Olay Active Beauty Fluid | 0.9 |
| 4 | Vaseline Intensive Care Dry Skin Lotion | 0.7 |
| 5 | Oil of Olay Active Beauty Fluid | 0.7 |
| 6 | Water | 50 |
| 7 | Water and Boots Aqueous Cream B.P. | 10 |
| 8 | Water | 3 |
| 9 | Oil of Olay Active Beauty Fluid | 2 |

Composition 1

30 g of TEAB was dissolved in 70 mL of water. This resulted in a composition with 30% by weight of TEAB.

Composition 2

3.0 g of composition 1 was manually dispersed in 97 g of the commercially-available skin treatment product Vaseline Intensive Care Dry Skin Lotion. This resulted in a composition with 0.9% by weight of TEAB.

Composition 3

3.0 g of composition 1 was manually dispersed in 97 g of the commercially-available skin treatment product Oil of Olay Active Beauty Fluid. This resulted in a composition with 0.9% by weight of TEAB.

Composition 4

2.3 g of composition 1 was manually dispersed in 97.7 g of the commercially-available skin treatment product Vaseline Intensive Care Dry Skin Lotion. This resulted in a composition with 0.7% by weight of TEAB.

Composition 5

2.3 g of composition 1 was manually dispersed in 97.7 g of the commercially-available skin treatment product Oil of Olay Active Beauty Fluid. This resulted in a composition with 0.7% by weight of TEAB.

Composition 6

50 g of TEAB was dissolved in 50 mL of water. This resulted in a composition with 50% by weight of TEAB.

Composition 7

20.0 g of composition 6 was manually dispersed in 80 g of the commercially-available skin moisturiser Boots Aqueous Cream B.P. This resulted in a composition with 10% by weight of TEAB.

Composition 8

3 g of TEAB was dissolved in 97 mL of water. This resulted in a composition with 3% by weight of TEAB.

Composition 9

2 g of TEAB was manually dispersed in 98 g of the commercially-available skin moisturiser Oil of Olay Active Beauty Fluid. This resulted in a composition with 2% by weight of TEAB.

Example 9

Eczema

Two male subjects and a female subject suffering from long-term genetically-acquired atopic eczema and related as biological father, grandson and daughter, were treated with composition 3. The TEAB composition was topically applied in a liberal manner by rubbing into an affected area of the skin around the ankles or the eyebrows of the subjects which was flaky, peeling and itchy.

Within three days post-treatment, the affected areas of skin had returned to a healthy state with no sign of flakiness, peeling or itchiness. At 12 months post-treatment, the eczema had not returned. At 16-months post-treatment, eczema returned in one of the subjects and was treated in the same manner as described above resulting in the affected areas of skin returning to their healthy state with no sign of flakiness, peeling or itchiness. Thus, for all subjects, topical application of the TEAB composition has shown effect as both a curative and preventative treatment of atopic eczema.

Example 10

Acne

A male subject suffering from severe facial acne was treated with composition 3. The TEAB composition was applied to selected areas of the facial skin with other affected areas not treated. A noticeable improvement of the subject's condition was observed 24 hours post-treatment with the acne clearing while the non-treated areas remained substantially unchanged. Within 6 days post-treatment, the acne had nearly cleared. After 14 days the acne was completely cleared and did not return. Thus, topical application of a TEAB composition has shown effect as both a curative and preventative treatment of acne.

Example 11

Flea Bite

An area of a male subject's legs was subjected to flea bites which resulted in a painful rash. A portion of skin on the leg having the rash was treated with a composition 3. Pain relief in the treated area was almost instant and within 24 hours post-treatment the rash was reduced to a milder pain-free rash on the treated area of the subject's leg. Further application of composition 3 resulted in disappearance of the rash within a further 24-hour interval.

In another study, an area of a male subject's legs previously treated with composition 3 was subjected to flea bites. In contrast to the painful rash observed as mentioned above, small, red, pain-free spots were observed for the pre-treated skin which disappeared after 2 days with further treatment as described above. Thus, topical application of a TEAB composition has shown effect as both a curative and preventative treatment of a painful rash caused by a flea bite.

Example 12

Geographic Tongue

A male subject suffering from geographic tongue was treated with composition 1. The composition was applied to the tongue and the tongue held firmly against the roof of the subject's mouth for at least 10 minutes post-application. This treatment was repeated at 24-hour intervals for a period of 1 week. During this 1-week period, the discomfort caused by the subject's geographic tongue was significantly reduced and by the end of the period had disappeared as had the bright red circles on the tongue symptomatic of this condition. Subsequent return of the geographic tongue condition was treated in the same manner with the same results. Thus, oral administration of a TEAB composition has shown effect as a curative treatment of geographic tongue.

Example 13

Psoriasis

Composition 7 was topically applied in a liberal manner by rubbing into an affected area of the skin of a male subject suffering from long- term psoriasis. Within 1 week, a significant improvement in the subject's condition was observed. Thus, topical application of a TEAB composition has shown effect as a curative treatment of psoriasis.

Prior to the initial treatment, composition 3 and composition 5 were separately applied to the affected area of the subject with no effect. Subsequently, composition 6 was applied to the affected area of the subject by spraying. This resulted in considerable pain and redness to the treated area which was ameliorated by treatment with composition 3 or composition 5. Thus, topical application of a TEAB composition has shown effect in ameliorating pain caused by an adverse reaction to an excessively high dosage of TEAB.

Example 14

Post-Nasal Drip

A female subject suffering from a combination of long-term postnasal drip was treated with composition 8. Treatment was by nasal spray with a single 0.25 to 0 5 mL dose of the solution sprayed as a mist into each nostril. Relief from post-nasal drip was observed within 15 minutes. Thus, nasal administration of a TEAB composition has shown effect in relieving the symptoms of post-nasal drip.

Example 15

Bruised Cheek and Eye

A male subject suffering from a bruised and swollen cheek and face surrounding the eye was treated with composition 9. The composition was applied liberally to the affected area by rubbing into the skin on the cheek and surrounding the eye. After 12 hours, the swelling was reduced by approximately half and the bruising had disappeared. Within 24 hours of a further application of the composition, the swelling had disappeared completely. Thus, topical application of a TEAB composition has shown effect in expediting the reduction of bruising and swelling which has resulted from a facial injury.

Example 16

Gout

A male subject suffering from gout in the big toe and having walking difficulties was treated with composition 9. The composition was applied liberally to the affected area of the toe by rubbing into the skin and area surrounding the toe nail. At 3 days post-treatment, the toe had returned to normal allowing pain-free walking. Thus, topical application of a TEAB composition has shown effect as a curative treatment for gout.

Example 17

Cold Sore

A female subject experiencing a pre-cold sore twinge on the upper lip was treated with composition 9. The composition was applied liberally to the affected area by rubbing into the upper lip and surrounding skin. After 12 hours, a small pain-free rash had developed and the twinge was no longer felt by the subject. Further 12-hourly application of the composition resulted in the rash disappearing after 2 days and no cold sore developing. Thus, topical application of a TEAB composition has shown effect as a curative and preventative treatment of a cold sore.

Example 18

Dry and Itchy Skin

A male subject suffering from localised patches of dry and itchy skin present on the chest was treated with composition 9. The composition was applied liberally to the affected areas. Relief from the itchiness was observed within 1 minute post-treatment. By 3 days post-treatment, the affected areas of skin had returned to a normal healthy state. Thus, topical application of a TEAB composition has shown effect in ameliorating irritation caused by dry and itchy skin.

Example 19

Scar Tissue

A male subject suffering from post-operation itchiness and inflammation of hip replacement scar tissue was treated with composition 9. The composition was applied liberally to the scar tissue and surrounding skin. Relief from the itchiness was observed within 1 minute post-application. Within 7 days post-application, the inflammation and associated redness of the scarred area had disappeared. Thus, topical application of a TEAB composition has shown effect in ameliorating itchiness and inflammation present on and around post-operative scar tissue.

Example 20

Injured Finger

The finger of a male subject painfully injured by a heavy blow which resulted in blood seeping between the cuticle and nail was treated with composition 1 followed by composition 9. Composition 1 was sprayed generously on to the area around the cuticle and composition 9 subsequently applied liberally to the area on and around the cuticle with a gentle rubbing motion. Within 12 hours post-application, the injured finger had returned to being pain-free with no bleeding evident. Thus, topical application of a TEAB composition has shown effect in ameliorating the pain and bleeding of an injury caused by a heavy blow to the finger.

Example 21

Steam Scald

A male subject suffering from a minor steam burn on the hand was treated with composition 1 followed by composition 9. Composition 1 was sprayed on to the burn and composition 9 subsequently applied liberally to the burn area by gentle rubbing into the skin. Within 1 minute post-application, the pain of the burn had subsided. Within 12 hours post-application, the burn had completely healed. Thus, topical application of a TEAB composition has shown effect in reducing the pain associated with a steam burn as well as expediting the healing of a wound caused by a burn.

Example 22

Sweet Itch

In the following Example, TEAB compositions were tested for efficacy on a horse susceptible to sweet itch.

A mare susceptible to sweet itch was treated successively with composition 1 and composition 7. Composition 1 was applied as a fine spray to the base of the mane and tail hair of the mare. This was followed by application of composition 7 to the same areas. Facial areas of the mare were not treated with a TEAB composition. Another horse sharing the same paddock as the mare and also susceptible to sweet itch was not treated.

After 3 days post-treatment, the untreated facial areas of the mare became affected by sweet itch. However the treated areas of the mare did not become affected by sweet itch. Furthermore, the untreated horse became affected by sweet itch. Thus, topical application of a TEAB composition has shown effect as a curative and preventative treatment for sweet itch in a horse.

Example 23

Bacterial Infection

Cultures of Pseudomonas aeruginosa, Escherichia coli, Staphylococcus aureus, Staphylococcus epidermis and Bacillus subtilis were prepared separately on Petri dishes containing an agar broth. Composition 6 was dropped into a well located in the centre of each culture dish. Within 72 hours post-treatment, partial bacterial kill was observed in each dish. Thus, a TEAB composition has shown effect as an anti-bacterial agent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for the topical treatment of infection, inflammation or pain in a human or an animal comprising an application of a therapeutically effective amount of a compound of formula (I) or a composition comprising a compound of formula (I) to the human or animal in need of such treatment, wherein formula (I) is represented by:

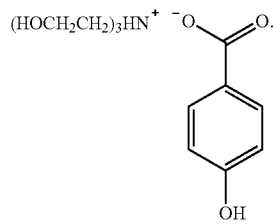
(I)

2. The method according to claim 1 wherein the treatment is for eczema, psoriasis, acne, sunburn, a wound, bruising, a burn, gout, ringworm, a cold sore, impetigo, a symptom associated with the common cold or influenza, gum disease, cystic fibrosis, epidermolysis bullosa, bacterial infection, geographic tongue, an adverse reaction to an insect bite or sweet itch.

3. The method according to claim 1, wherein the compound or composition is applied to an area of the human or animal to be treated by:

(i) rubbing the composition into the area to be treated, or (ii) spraying an aqueous composition of the compound of formula (I) onto the area to be treated.

4. The method according to claim 1, wherein the method comprises applying the composition comprising the compound of formula (I).

5. The method according to claim 4, wherein the compound according formula (I) is present up to 60% by weight of the composition.

6. The method according to claim 4, wherein the compound according to formula (I) is present at 0.2 to 10% by weight of the composition.

7. The method according to claim 4, wherein the composition comprises a pharmaceutically acceptable carrier.

8. The method according to claim 4, wherein the composition comprises glycerol.

* * * * *